(12) United States Patent  
Satake

(10) Patent No.: US 8,226,637 B2  
(45) Date of Patent: Jul. 24, 2012

(54) BALLOON CATHETER SYSTEM

(75) Inventor: Shutaro Satake, Kanagawa (JP)

(73) Assignee: Japan Electel, Inc., Tokyo (JP)

(*) Notice: Subject to any disclaimer, the term of this patent is extended or adjusted under 35 U.S.C. 154(b) by 1121 days.

(21) Appl. No.: 12/091,967

(22) PCT Filed: Nov. 1, 2005

(86) PCT No.: PCT/JP2005/020140
§ 371 (c)(1),
(2), (4) Date: Apr. 29, 2008

(87) PCT Pub. No.: WO2007/052341
PCT Pub. Date: May 10, 2007

(65) Prior Publication Data
US 2009/0157066 A1    Jun. 18, 2009

(51) Int. Cl.
*A61B 18/08* (2006.01)
(52) U.S. Cl. .................... 606/28; 606/41; 604/509
(58) Field of Classification Search .......... 606/27–31, 606/41–50; 600/115, 116; 604/509
See application file for complete search history.

(56) References Cited

U.S. PATENT DOCUMENTS

| | | | | |
|---|---|---|---|---|
| 5,571,153 A | * | 11/1996 | Wallsten | 607/98 |
| 2003/0195510 A1 | * | 10/2003 | Schaer | 606/41 |
| 2004/0006333 A1 | | 1/2004 | Arnold et al. | |
| 2004/0147915 A1 | * | 7/2004 | Hasebe | 606/28 |
| 2004/0172110 A1 | * | 9/2004 | Satake | 607/101 |

FOREIGN PATENT DOCUMENTS

| | | | |
|---|---|---|---|
| JP | 09-192227 A | | 7/1997 |
| JP | 2002-011101 A | | 1/2002 |
| JP | 2003-144553 A | | 5/2003 |
| JP | 2003144553 | * | 5/2003 |
| JP | 2004-223080 A | | 8/2004 |
| JP | 2005-058507 A | | 3/2005 |
| JP | 2005-177293 A | | 7/2005 |
| JP | 3705832 B2 | | 8/2005 |
| WO | 00/56237 A2 | | 9/2000 |

* cited by examiner

*Primary Examiner* — Michael Peffley
*Assistant Examiner* — Samantha Good
(74) *Attorney, Agent, or Firm* — McDermott Will & Emery LLP

(57) ABSTRACT

There is provided a balloon catheter system, enabling only a target site to be efficiently ablated, ensuring a balloon to be able to be brought into close contact with the target site in conformity to a shape of the target site. A balloon includes a contact portion that is to contact a target site and a noncontact portion that is not to contact the target site. A membrane thickness of the contact portion is thinner than that of the noncontact portion. Then, the target site that is in contact with the thin contact portion is selectively ablated, while making heat leak from the thick noncontact portion less likely to occur. Hence, only the target portion can be efficiently ablated.

11 Claims, 9 Drawing Sheets

BALLOON CATHETER SYSTEM

CROSS-REFERENCE TO PRIOR APPLICATIONS

This is a U.S. national phase application under 35 U.S.C. §371 of International Patent Application No. PCT/JP2005/020140, filed Nov. 1, 2005, which is incorporated by reference herein. The International Application was published in Japanese on May 10, 2007 as International Publication No. WO 2007/052341 A1 under PCT Article 21(2).

TECHNICAL FIELD

The present invention relates to a balloon catheter system, particularly to a balloon catheter system for thermotherapy that is used for treating cardiovascular diseases.

BACKGROUND

A method is proposed in which, with respect to lesions such as an origin of arrhythmia or atherosclerosis, an electrode for delivery of radiofrequency energy is arranged inside an elastic balloon, and a radiofrequency electric field is radiated therefrom, to provide thermotherapy to a tissue in contact with the balloon (for example, refer to Patent Document 1).

Patent Document 1: Japanese Unexamined Patent Publication No.: 2005-177293

In order to provide uniform thermotherapy to a target site to be treated inside a blood vessel and a heart, it is necessary to bring a balloon into close contact with the target site and then block a blood flow to thereby selectively heat and ablate the target site. According to the conventional balloon catheters, however, a wall thickness of the balloon is uniform, and thus there is concern of isolating a site different from the target site. Further, thermal energy inside the balloon leaks from a portion that is not in contact with the target site, resulting in poor heating efficiency.

Furthermore, there has been a problem that a position of the target site is subjected to changes by a pulsation of the heart and the blood flow, and thus it is difficult to bring the balloon into close contact with the target site only by pressurizing the inside of the balloon to change a diameter of the balloon.

With the view of the problems described above, it is, therefore, an object of the present invention to provide a balloon catheter system which enables only the target site to be effectively ablated, enabling the balloon to be brought into close contact with the target site by conforming to a shape of the target site.

SUMMARY

To attain the objects described above, a first aspect of the present invention is a balloon catheter system comprising: a catheter shaft comprising an outer tube and an inner tube; an elastic balloon provided between a distal end of said outer tube and a vicinity of a distal end of said inner tube; a heating element provided inside said balloon; a temperature sensor which detects a temperature inside said balloon; a solution transport path formed between said outer tube and said inner tube, in communication with an inside of said balloon; a vibration generator which applies vibrational waves to said balloon through said solution transport path; and a vibrational wave baffle which deflects said vibrational wave inside said balloon, wherein said balloon includes a contact portion that is to contact a target site and a noncontact portion that is not to contact said target site, said contact portion having a membrane thickness less than that of said noncontact portion.

A second aspect of the present invention is a balloon catheter system in which in the first aspect, said heating element is any one of a radiofrequency electrode, a nichrome wire, an infrared ray generator, a heat emitting diode, a laser irradiator and an ultrasonic wave generator.

A third aspect of the present invention is a balloon catheter system in which in the first aspect, the balloon is formed in conformity to a shape of the target site.

A fourth aspect of the present invention is a balloon catheter system in which in the third aspect, the balloon is substantially sphere-shaped or substantially onion-shaped and the contact portion is provided in the vicinity of the distal portion of the balloon.

A fifth aspect of the present invention is a balloon catheter system in which in the third aspect, said balloon includes a spherical portion fixed to the distal end of said outer tube and a cylindrical portion that extends from said spherical portion and is fixed to the distal end of said inner tube, while said contact portion is provided in the vicinity of the distal portion of said spherical portion, and said cylindrical portion is formed to have a less thickness at the distal portion thereof than at the proximal portion thereof.

A sixth aspect of the present invention is a balloon catheter system in which in the third aspect, the balloon is substantially cylindrically-shaped and the contact portion is provided in the vicinity of a central portion of the balloon.

A seventh aspect of the present invention is a balloon catheter system in which in the first aspect, said outer tube and said inner tube are constituted in a manner capable of sliding with each other so that a length of said balloon is changed by varying a distance between the distal end of said outer tube and the distal end of said inner tube, while a diameter of said balloon is changed by varying pressure of solution supplied to said balloon.

An eighth aspect of the present invention is a balloon catheter system in which in the first aspect, there is further provided a distance regulating device at the proximal portion of the catheter shaft, which regulates a distance between the distal portion of the inner tube and the distal portion of the outer tube.

A ninth aspect of the present invention is a balloon catheter system in which in the eighth aspect, said distance regulating device includes an internally-threaded portion fixed to a proximal end of said outer tube, a fixing valve that is provided inside said internally-threaded portion and has said inner tube inserted therethrough, and a rotating knob provided with an externally-threaded portion which engages with said internally-threaded portion and tightens said fixing valve, whereby said fixing valve is elastically deformed when said rotating knob is rotated to tighten said fixing valve so that said inner tube is fixed to said internally-threaded portion.

A tenth aspect of the present invention is a balloon catheter system in which in the ninth aspect, the distance regulating device includes an indicating needle fixed to the inner tube inside the rotating knob, and the rotating knob is formed in a frame shape to limit a movable range of the indicating needle within an internal side of the rotating knob.

An eleventh aspect of the present invention is a balloon catheter system in which in the tenth aspect, the rotating knob is provided with a scale indicating the distance between the distal portion of the outer tube and the distal portion of the inner tube by means of a position of the indicating needle.

A twelfth aspect of the present invention is a balloon catheter system in which in the seventh aspect, there are further provided a first lead wire connected to said heating element and a second lead wire connected to said temperature sensor, wherein said heating element and said temperature sensor are fixed to the distal end of said inner tube, while said first lead wire and said second lead wire are fixed to said inner tube between the distal end of said inner tube and the proximal portion thereof.

A thirteenth aspect of the present invention is a balloon catheter system in which in the first aspect, said heating element is a radiofrequency electrode, while said temperature sensor is a thermocouple, said balloon catheter system further comprising: a radiofrequency generator which feeds a radiofrequency current to said radiofrequency electrode; a thermometer which indicates a temperature detected by said thermocouple; a low-frequency band cut filter that is provided between said radiofrequency electrode and said radiofrequency generator and cuts off low-frequency components of the radiofrequency waves output from said radiofrequency generator; a radiofrequency band cut filter that is provided between said thermocouple and said thermometer and cuts off radiofrequency components input to said thermometer; and a lead wire that connects said thermocouple with said radiofrequency band cut filter, whereby said radiofrequency current is fed to said radiofrequency electrode through said lead wire.

A fourteenth aspect of the present invention is a balloon catheter system comprising: a catheter shaft comprising an outer tube and an inner tube; a balloon provided between a distal end of said outer tube and a distal end of said inner tube; a heating element provided inside said balloon; a temperature sensor which detects a temperature inside said balloon; and a solution transport path formed between said outer tube and said inner tube, in communication with an inside of said balloon, wherein said balloon includes a contact portion that is to contact a target site and a noncontact portion that is not to contact said target site, said noncontact portion being provided with a heat insulating layer.

According to the balloon catheter system of the first aspect of the present invention, the balloon is heated by the heating element, while the balloon catheter system includes the vibration generator for applying a vibrational wave to the balloon through the solution transport path and the vibrational wave baffle for deflecting the vibrational wave inside the balloon. Accordingly, solution inside the balloon is agitated by the vibrations polarized to make a temperature distribution of the solution uniform inside the balloon. Further, the balloon includes a contact portion that is to contact the target site and a noncontact portion that is not to contact the target site, and besides a membrane thickness of the contact portion is thinner than that of the noncontact portion. Hence, the target site that is in contact with the thin contact portion is selectively heated, making the heat leak from the thick noncontact portion less likely to occur, thus permitting only the target site to be efficiently and uniformly ablated.

According to the balloon catheter system of the second aspect of the present invention, any one of a radiofrequency electrode, a nichrome wire, an infrared ray generator, a heat emitting diode, a laser irradiator and an ultrasonic generator can be employed as the heating element. Hence, a wide variety of heat emitting bodies is applicable.

According to the balloon catheter system of the third aspect of the present invention, the balloon is formed in conformity to a shape of the target site. Hence, the balloon can be brought into close contact with the target site with certainty.

According to the balloon catheter system of the fourth aspect of the present invention, the balloon is substantially sphere-shaped or substantially onion-shaped, and the contact portion is provided in the vicinity of the distal portion of the balloon. Hence, the target site can be ablated in the vicinity of the distal portion of the balloon.

According to the balloon catheter system of the fifth aspect of the present invention, said balloon includes a spherical portion fixed to the distal end of said outer tube and a cylindrical portion that extends from said spherical portion and is fixed to the distal end of said inner tube, while said contact portion is provided in the vicinity of the distal portion of said spherical portion, and said cylindrical portion is formed to have a smaller membrane thickness at the distal portion thereof than at the proximal portion thereof. Hence, by pressurizing the inside of the balloon, the distal portion of the balloon is extended to fix the cylindrical portion to an inside of a blood vessel with certainty, so that the target site at the circumference of a blood vessel ostium can be ablated with certainty.

According to the balloon catheter system of the sixth aspect of the present invention, the balloon is substantially cylindrically-shaped and the contact portion is provided in the vicinity of a central portion of the balloon. Hence, the target portion can be ablated in the vicinity of the central portion of the balloon.

According to the balloon catheter system of the seventh aspect of the present invention, the outer tube and the inner tube are constituted so as to be slidable with respect to each other, and the length of the balloon changes by varying the distance between the distal portion of the outer tube and the distal portion of the inner tube, while the diameter of the balloon changes by varying the pressure of the solution supplied to the balloon. Hence, the length and diameter of the balloon are changed in conformity to a shape of the target site, permitting the balloon to be brought into close contact with target site.

According to the balloon catheter system of the eighth aspect of the present invention, there is provided the distance regulating device for regulating the distance between the distal portion of the outer tube and the distal portion of the inner tube at the proximal portion of the catheter shaft. Hence, the length of the balloon can be regulated.

According to the balloon catheter system of the ninth aspect of the present invention, said distance regulating device includes an internally-threaded portion fixed to a proximal end of said outer tube, a fixing valve that is provided inside said internally-threaded portion and has said inner tube inserted therethrough, and a rotating knob provided with an externally-threaded portion which engages with said internally-threaded portion and tightens said fixing valve, whereby said fixing valve is elastically deformed when said rotating knob is rotated to tighten said fixing valve so that said inner tube is fixed to said internally-threaded portion. Hence, with a simple operation, the inner tube can be fixed to an appropriate position relative to the outer tube.

According to the balloon catheter system of the tenth aspect of the present invention, said distance regulating device includes an indicating needle fixed to said inner tube inside said rotating knob, said rotating knob being formed in a frame shape to limit a movable range of said indicating needle within an internal side of said rotating knob. Hence, the movable range of the inner tube in relation to the outer tube can be kept within an appropriate range.

According to the balloon catheter system of the eleventh aspect of the present invention, the rotating knob is provided with a scale indicating the distance between the distal portion of the outer tube and the distal portion of the inner tube according to a position of the indicating needle. Hence, the balloon can be precisely set in length.

According to the balloon catheter system of the twelfth aspect of the present invention, there are further provided a first lead wire connected to said heating element and a second lead wire connected to said temperature sensor, wherein said heating element and said temperature sensor are fixed to the distal end of said inner tube, while said first lead wire and said second lead wire are fixed to said inner tube between the distal end of said inner tube and the proximal portion thereof. Hence, when the outer tube and the inner tube are allowed to slide with each other, the first wire and the second wire can be prevented from becoming entwined with each other.

According to the balloon catheter system of the thirteenth aspect of the present invention, said heating element is a radiofrequency electrode, while said temperature sensor is a thermocouple, said balloon catheter system further comprising: a radiofrequency generator which feeds a radiofrequency current to said radiofrequency electrode; a thermometer which indicates a temperature detected by said thermocouple; a low-frequency band cut filter that is provided between said radiofrequency electrode and said radiofrequency generator and cuts off low-frequency components of the radiofrequency waves output from said radiofrequency generator; a radiofrequency band cut filter that is provided between said thermocouple and said thermometer and cuts off radiofrequency components input to said thermometer; and a lead wire that connects said thermocouple with said radiofrequency band cut filter, whereby said radiofrequency current is fed to said radiofrequency electrode through said lead wire. Hence, only the radiofrequency components are output from the radiofrequency generator, while only the low-frequency components are input to the thermometer, and thus the radiofrequency electrode and the thermocouple share the lead wire, enabling the radiofrequency power supply and the temperature detection to be performed at the same time.

According to the balloon catheter system of the fourteenth aspect of the present invention, the balloon includes a contact portion that is to contact the target site and a noncontact portion that is not to contact the target site, while a heat insulating layer is provided in the noncontact portion. Hence, heat is made less likely to leak from the noncontact portion provided with the heat insulating layer, enabling only the target site to be efficiently and selectively ablated.

DETAILED DESCRIPTION

The following is a detailed description of a balloon catheter system according to the present invention taking, as an example, a balloon catheter system used for electrically isolating an ostium of pulmonary vein for treatment of atrial fibrillation, with reference to the appended drawings.

Embodiment 1

A first embodiment of a balloon catheter system according to the present invention is shown in FIG. 1 to FIGS. 5A-5B are.

Figure 1:
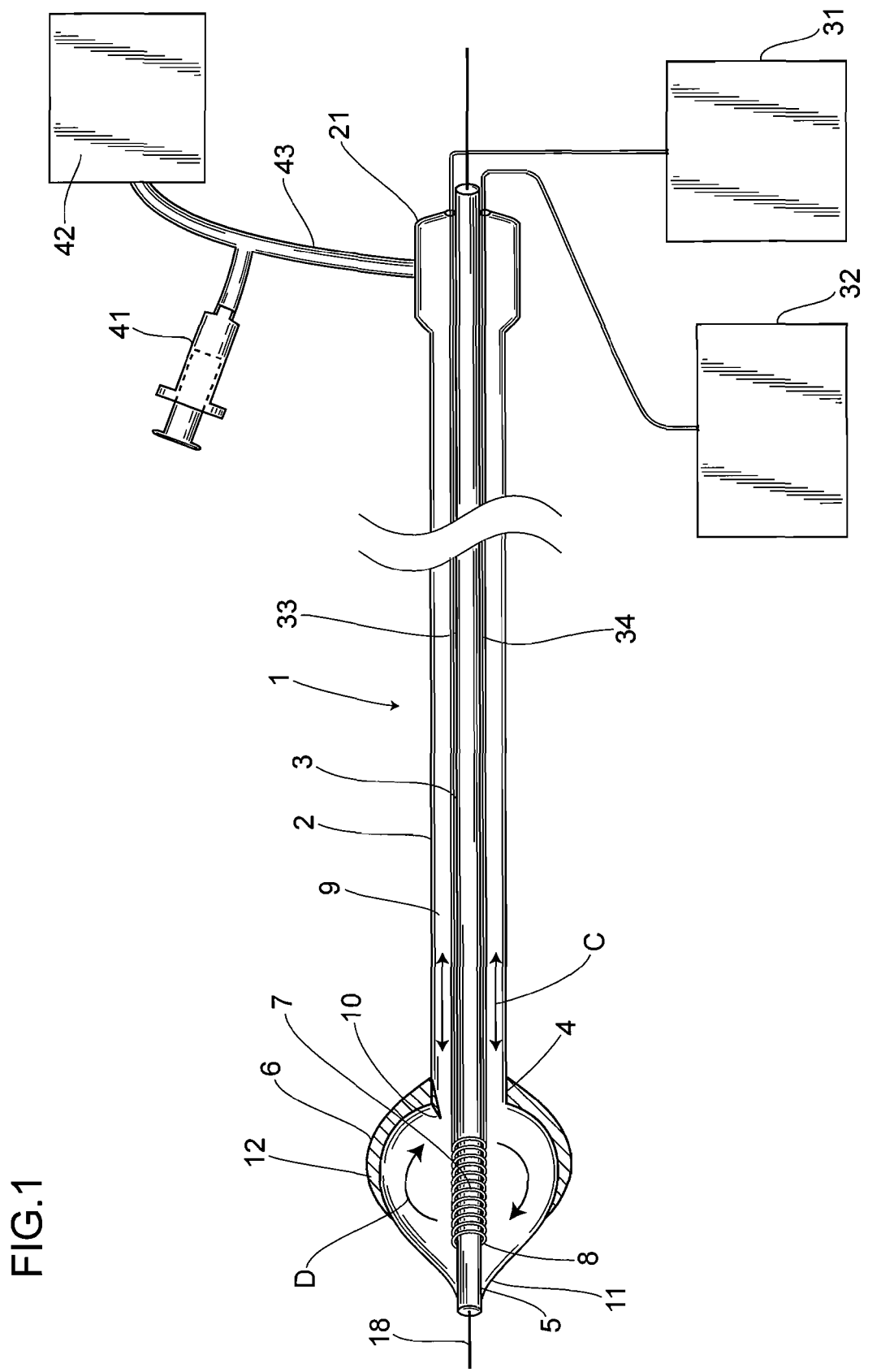
FIG. 1 is an overall view illustrating a first embodiment of a balloon catheter system according to the present invention.
Figure 2:
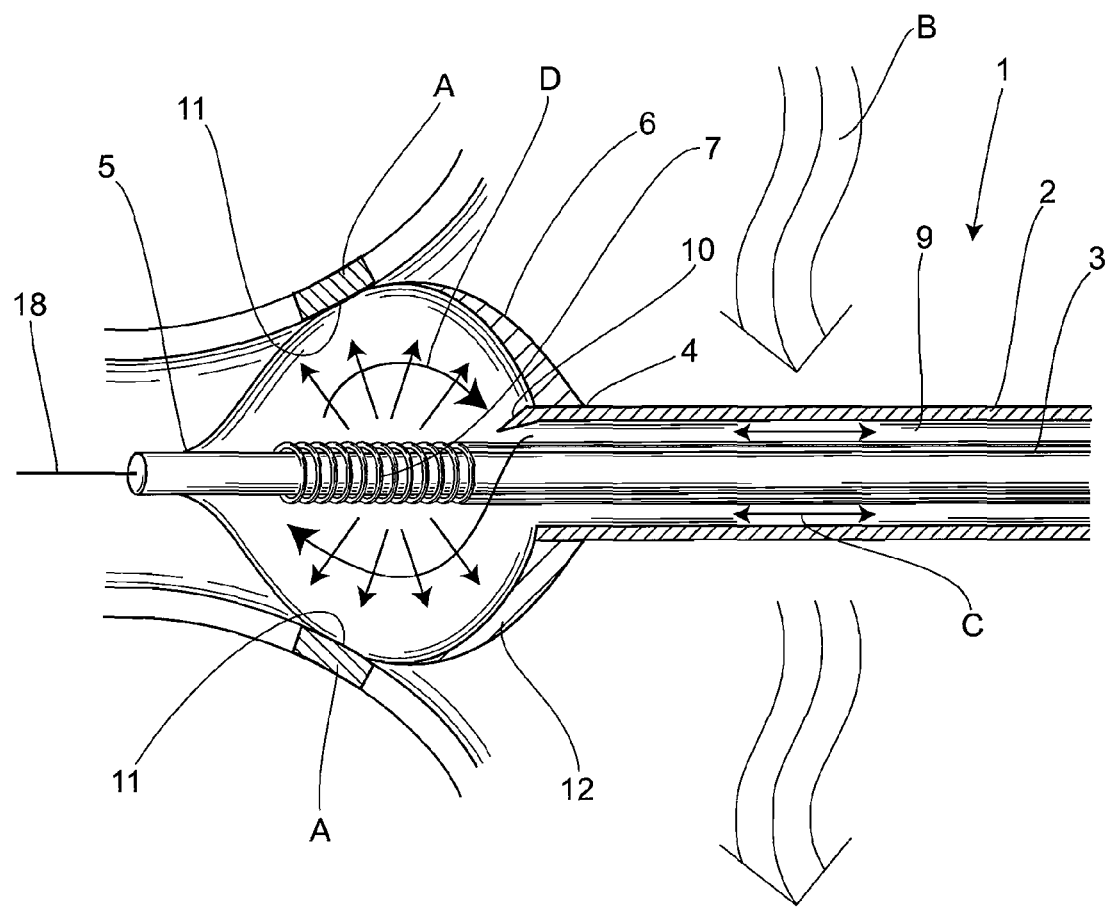
FIG. 2 is a partially enlarged view illustrating the vicinity of a balloon of the first embodiment thereof.
Figure 3:
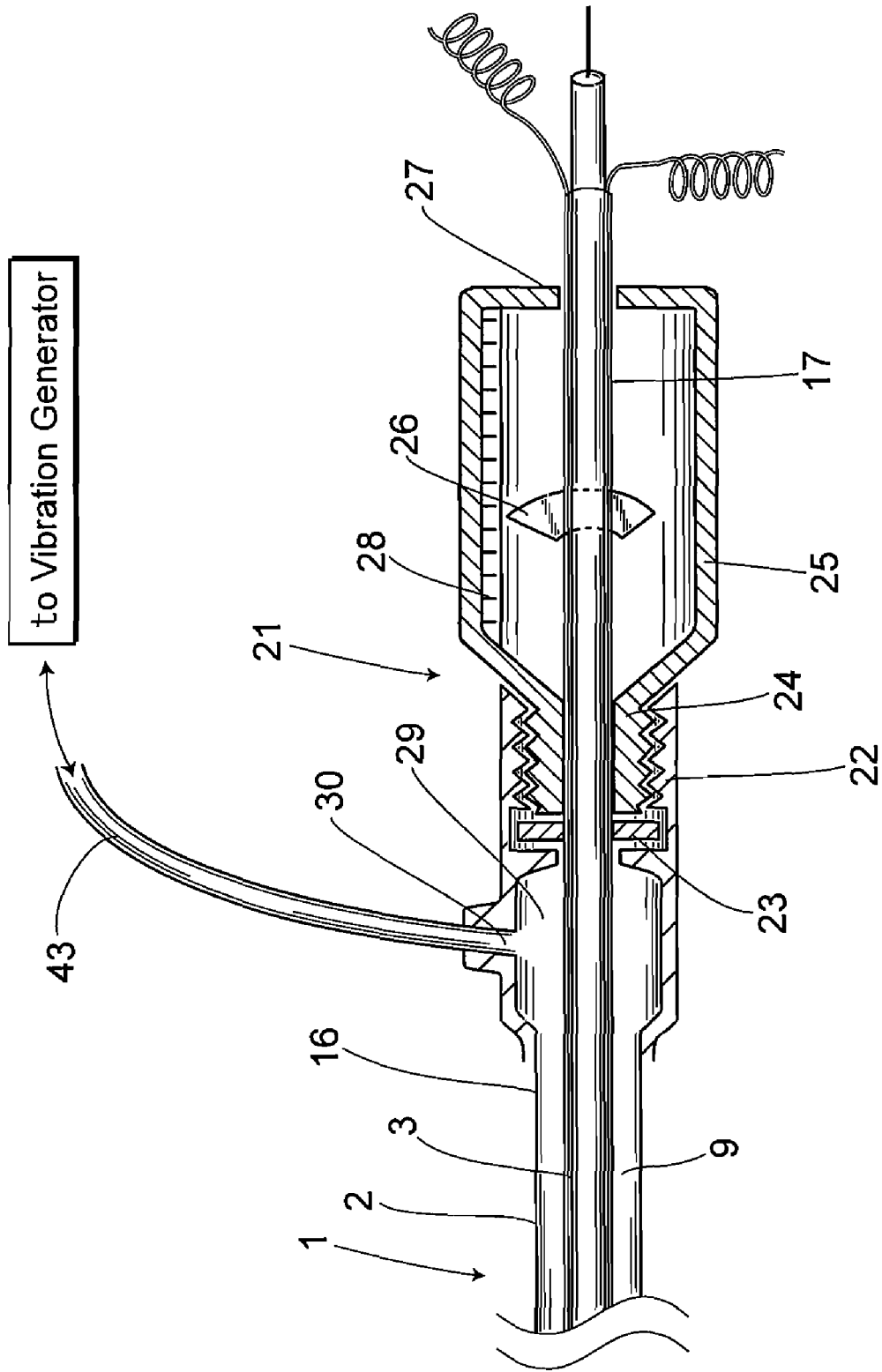
FIG. 3 is a partially enlarged view, showing a distance regulating device of the first embodiment thereof.

First, with reference to FIG. 1 to FIG. 3, a description is given for a structure of the balloon catheter system according to the present embodiment. Numeral symbol 1 denotes a catheter shaft, which comprises an outer tube 2 and an inner tube 3 which are slidable with each other. A balloon 6 is provided between a distal portion 4 of the outer tube 2 and a distal portion 5 of the inner tube 3. A radiofrequency electrode 7 acting as a heating element and a thermocouple 8 acting as a temperature sensor for detecting temperature are provided inside the balloon 6 and at a distal portion of the radiofrequency electrode 7, respectively. Further, a solution transport path 9 communicating with an inside of the balloon 6 is formed between the outer tube 2 and the inner tube 3.

The balloon 6 includes a contact portion 11 that is to contact a target site A of an ostium of a pulmonary vein and a noncontact portion 12 that is not to contact the target site A. A membrane thickness of the contact portion 11 is formed thinner than that of the noncontact portion 12. The balloon 6 is formed from synthetic resin such as polyurethane or the like, and the contact portion 11 and the noncontact portion 12 are formed to a membrane thickness of 0.1 to 0.2 mm and 0.2 to 0.4 mm, respectively. Due to the membrane thickness being thus provided, heat inside the balloon 6 can be prevented from leaking from the noncontact portion 12 to the outside, allowing only the target site A in contact with the contact portion 11 to be effectively heated and ablated.

Preferably, the balloon 6 is formed in conformity to a shape of the target portion A based on a CT image or an MRI image of the target site A in the ostium of the pulmonary vein. By doing so, the balloon 6 can be brought into close contact with the target site A and thus it can completely block a blood flow B in the ostium of the pulmonary vein, so that the target site A can be effectively heated. According to the present embodiment, the balloon 6 is formed in an onion shape and the contact portion 11 is provided in the vicinity of the distal portion of the balloon 6. Therefore, the balloon 6 is brought into close contact with the target site A and thus completely blocks the blood flow B in the ostium of the pulmonary vein, so that the target site A can be effectively heated. Alternatively, the shape of the balloon 6 for heating the target site A may be substantially spherical instead of being onion-shaped.

According to the present embodiment, the heating element is constituted by the radiofrequency electrode 7 fixedly coiled around the vicinity of the distal portion 5 of the inner tube 3, which, however, is not limited to any specific one as long as it is capable of heating the inside of the balloon 6, and thus any of a nichrome wire, an infrared ray generator, a heat emitting diode, a laser irradiator and an ultrasonic generator may be applicable. Further, the thermocouple 8 is fixed to the vicinity of the distal portion 5 of the inner tube 3.

On a proximal portion of the catheter shaft 1 is provided a distance regulating device 21 that regulates a distance between the distal portion 4 of the outer tube 2 and the distal portion 5 of the inner tube 3. The distance regulating device 21 includes an internally threaded portion 22 fixed to the proximal portion 16 of the outer tube 2, a fixing valve 23 which is provided inside the internally threaded portion 22 and has the inner tube 3 inserted therethrough, and a rotating knob 25 provided with an externally threaded portion 24 which engages with the internally threaded portion 22 to tighten the fixing valve 23. The rotating knob 25 is formed in a frame shape, and when rotating the rotating knob 25 to tighten the fixing valve 23, the inner tube 3 becomes fixed to the internally threaded portion 22. In the meantime, the fixing valve 23 is formed in a doughnut shape, using flexible synthetic resin. When it is tightened, the fixing valve 23 is elastically deformed to decrease the diameter of an ostium of the fixing valve 23 and thus presses the outer periphery of the inner tube 3.

Besides, the distance regulating device 21 includes an indicating needle 26 inside the rotating knob 25 formed in a frame shape. The rotating knob 25 includes an externally threaded portion 24 at one end thereof and a support 27 supporting the inner tube 3 at the other end thereof. A proximal portion 17 of the inner tube 3 penetrates the external threaded portion 24 and the support 27 so that it is supported by both ends of the rotating knob 25. Further, the indicating needle 26 is fixed to the inner tube 3 inside the rotating knob 25. The indicating needle 26 is formed larger than the holes of the external threaded portion 24 and support 27 which are penetrated by the inner tube 3. Accordingly, a movable range of the indicating needle 26 is limited to an internal side of the rotating knob 25, i.e., within a portion between the external threaded portion 24 and the support 27. Further, the rotating knob 25 includes a scale 28 which indicates a distance between the distal portion 4 of the outer tube 2 and the distal portion 5 of the inner tube 3 according to a position of the indicating needle 26. Thus, the length of the balloon 6 is changed by varying the distance between the distal portion 4 of the outer tube 2 and the distal portion 5 of the inner tube 3 by means of the distance regulating device 21. Outside the catheter shaft 1, there are provided a radiofrequency generator 31 acting as an energy generator for supplying an energy source to the radiofrequency electrode 7; and a thermometer 32 displaying the temperature detected by the thermocouple 8. Then, the radiofrequency electrode 7 and the radiofrequency generator 31 are electrically connected to each other by a first lead wire 33, while the thermocouple 8 and the thermometer 32 are electrically connected to each other by a second lead wire 34.

Further, the first lead wire 33 and the second lead wire 34 are fixed to the inner tube 3 between the distal portion 5 of the inner tube 3 and the proximal portion 17 thereof. With the structure thus made, when the inner tube 3 and the outer tube 5 are allowed to slide with each other, the first lead wire 33 and the second lead wire 34 are prevented from becoming entwined with each other.

Furthermore, outside the catheter shaft 1, there are provided a syringe 41 acting as a solution transport means for feeding solution to the balloon 6 through the solution transport path 9; and a vibration generator 42 for applying a vibrational wave C to the balloon 6 through the solution transport path 9. A solution transport anterior chamber 29 communicating with the solution transport path 9 is provided integrally with the internally threaded portion 22 between the proximal portion 16 of the outer tube 2 and the internally threaded portion 22. Besides, the solution transport anterior chamber 29 is provided with a solution transport ostium 30 for feeding solution from a lateral side of the solution transport anterior chamber 29, while a solution transport pipe 43 is connected with the solution transport ostium 30. The solution transport pipe 43 branches off in midstream and then the syringe 41 and the vibration generator 42 are coupled to the solution transport ostium 30 via the solution transport pipe 43. Then, by varying the pressure of the solution fed to the balloon 6 by means of the syringe 41, the diameter of the balloon 6 is changed. In the meantime, although the syringe 41 is employed as a solution transport means in the present embodiment, it shall not be limited to any specific device, as long as it is capable of feeding solution. For example, a syringe pump or any other types of pumps may be applicable thereto.

The solution transport anterior chamber 29 and the solution transport path 9 each have a sufficient volume to propagate the vibrational wave from the vibrational wave baffle 10 to the balloon 6. Besides, inside the balloon 6, there is provided the vibrational wave baffle 10 for deflecting the vibrational wave C propagated from the vibration generator 42 to the balloon 6 via the solution transport pipe 43 and the solution transport path 9. The vibrational wave baffle 10 is tabular and protrudes from the distal portion 4 of the outer tube 2 and is located at an angle directed toward a center of the balloon 6, so that the vibrational wave C from the solution transport path 9 is deflected to cause an eddy current D inside the balloon 6. Then, due to the structure thus formed, the solution inside the balloon 6 is agitated, keeping the temperature inside the balloon 6 uniform.

Also, there is provided a guide wire 18 which guides the catheter shaft 1 to the target site A at the ostium of the pulmonary vein with the inner tube 3 being penetrated by the guide wire 18.

Figure 4:
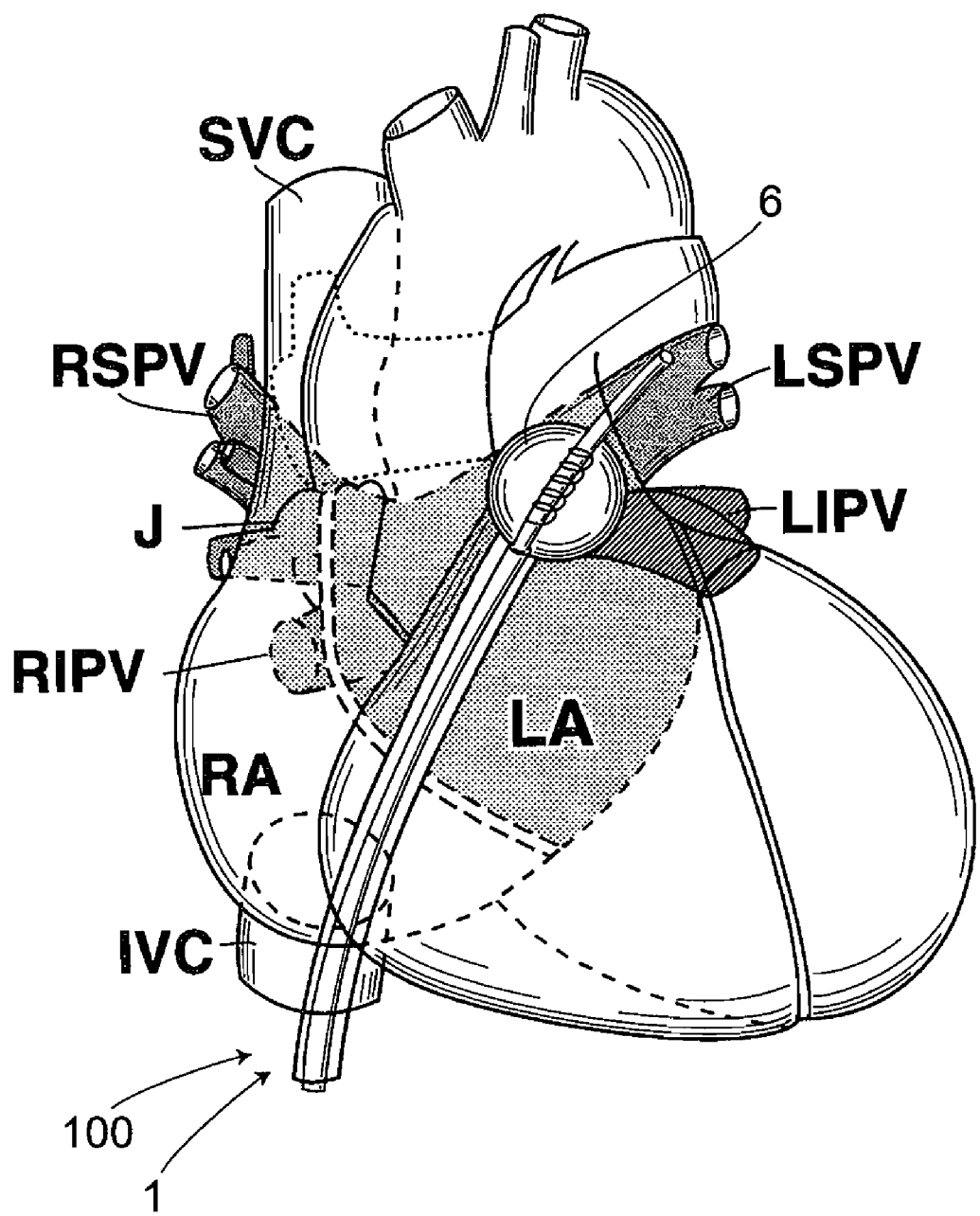
FIG. 4 is a diagram illustrating how the balloon catheter system of the first embodiment is actually used.
Figure 5A:
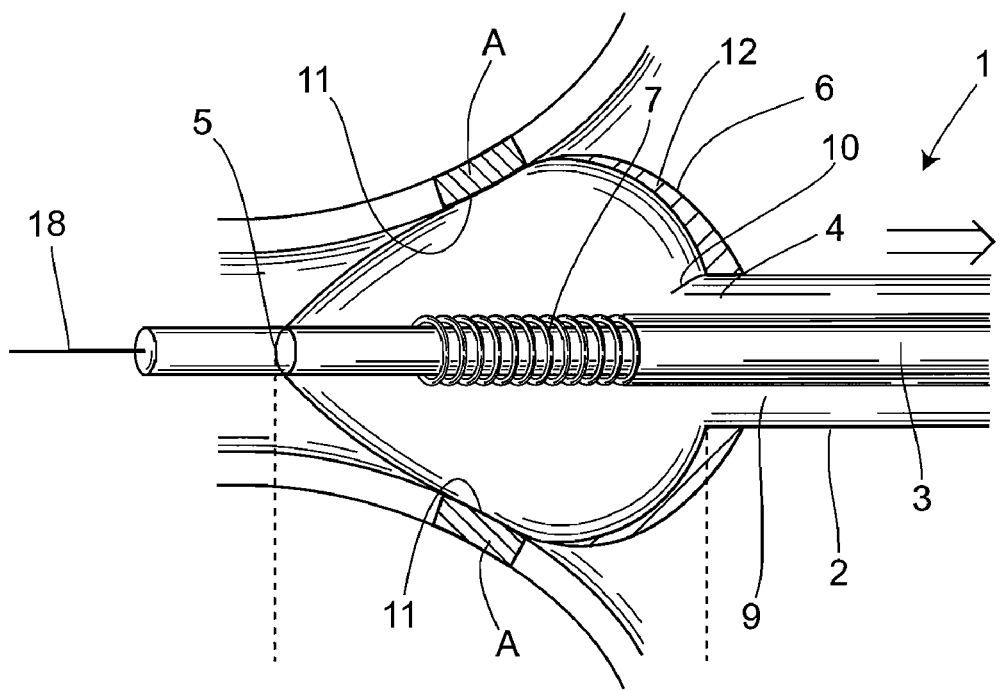
FIG. 5 is a partially enlarged view showing the vicinity of the balloon of the first embodiment in actual use.
Figure 5B:
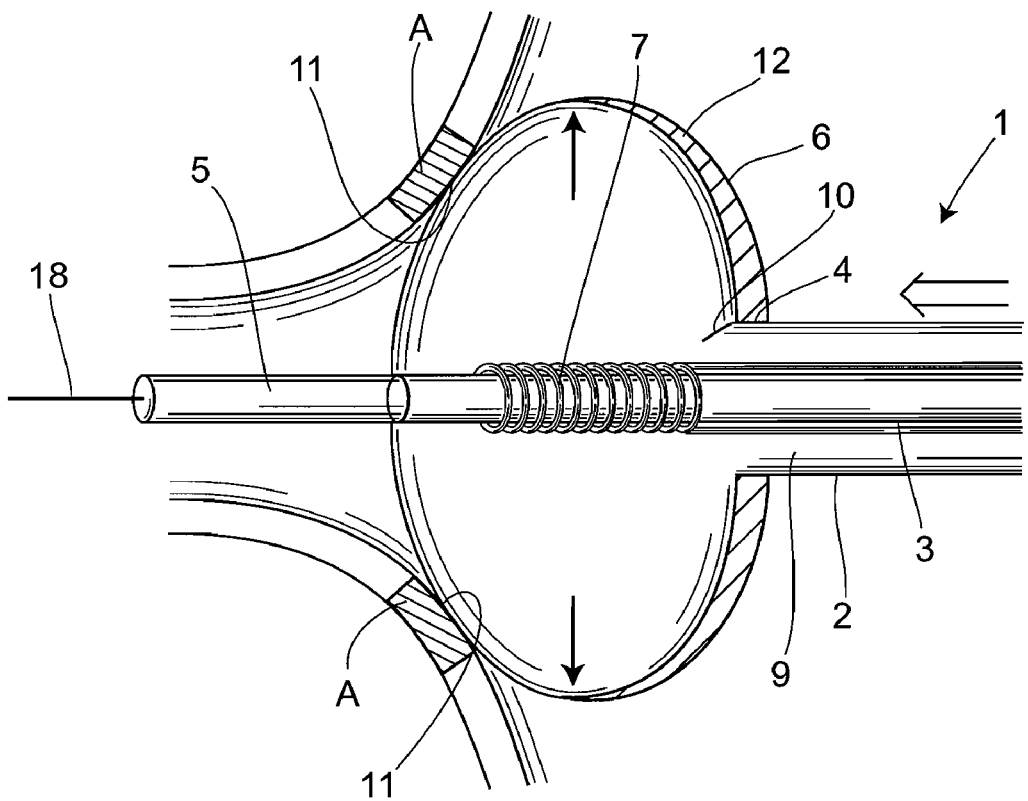

Next is a description of how to use the balloon catheter system of the present embodiment, taking for example a case of performing electrical isolation of an ostium of an upper left pulmonary vein, with reference to FIG. 4 and FIG. in addition to FIG. 1 to FIG. 3.

First, fluids such as physiological saline and a contrast medium are infused from the fluid feeding pipe 43 into an inside of a catheter lumen, i.e., the fluid feeding anterior chamber 29, the fluid feeding path 9 and the balloon 6, thus degassing the insides thereof. Then, with the inner tube 2 and the outer tube 3 being slid with each other so as to maximize the distance between the distal portion 4 of the outer tube and the distal portion 5 of the inner tube 3, the rotating knob 25 is turned to tighten the fixing valve 23, thereby fixing the inner tube 3 and then contracting the balloon 6.

A guiding sheath 100 for introducing the catheter shaft 1 from a femoral vein to a left atrium LA via an inferior vena cava IVC and a right atrium RA is inserted into a left atrium LA using the guide wire 18. Then, the deflated balloon 6 is inserted into the guiding sheath 100 to leave the balloon 6 in a left superior pulmonary vein LSPV.

Here, the fixing valve 23 is loosened and the inner tube 3 is allowed to slide, observing the indicating needle 26 and is stopped at an appropriate position where the fixing valve 23 is tightened. Then, the contrast medium is infused from the solution transport pipe 43 to inflate the balloon 6.

At this stage, in the case that the length of the balloon 6 is to be regulated, the distance between the distal portion 4 of the outer tube 2 and the distal portion 5 of the outer tube 3 is regulated by the distance regulating device 21. When the distance between the distal portion 4 of the outer tube 2 and the distal portion 5 of the inner tube 3 is regulated so as to be elongated, the balloon 6 is elongated as shown in an upper position in FIG. 5, whilst when it is regulated so as to be shortened, the balloon 6 is shortened as shown in a lower position in FIG. 5. Further, for regulating the diameter of the balloon 6, the pressure of the contrast medium supplied to the balloon 6 by the syringe 41 is regulated. In this way, the size of the balloon 6 is regulated, thus ensuring the contact portion 11 of the balloon 6 to come in contact with the target site A.

Then, the balloon 6 that has been regulated appropriately both in length and in diameter is pressed against the target site A adjacent to the left atrium LA in the ostium of the left superior pulmonary vein LSPV.

Subsequently, the first and second lead wires 33, 34 connected to the radiofrequency electrode 7 and the thermocouple 8, respectively from the proximal portion 17 of the inner tube 3 are connected to the radiofrequency generator 31 and the thermometer 32, respectively. Then, output from the radiofrequency generator 31 is increased while observing the thermometer 32. At the same time, the solution transport pipe 43 is connected to the vibration generator 42 to feed the vibrational wave C of 2 Hz to the inside of the balloon 6. Then, the catheter shaft 1 is rotated to regulate the orientation of the vibrational wave baffle 10, so that the vertical eddy current D is generated inside the balloon 6 to eliminate the nonuniformity of the temperature distribution inside the balloon 6.

Next, the diameter of the balloon 6 is measured to set a center temperature of the balloon 6 and a delivery time of energy in accordance with the diameter measured. When the diameter of the balloon 6 is 25 mm, for example, the temperature of the contact portion 11 that is to contact the target site A becomes 65 deg C. if a center temperature of the balloon 6 is held at 77 deg C. so that the target site A adjacent to the left atrium LA in the ostium of the left superior pulmonary vein LSPV is circumferentially ablated by delivery of energy for about 5 minutes to thereby electrically isolate the left superior pulmonary vein ostium LSPV from the left atrium LA.

In a similar fashion, electrically isolating the ostia of the remaining three pulmonary veins: a left inferior pulmonary vein LIPV, a right superior pulmonary vein RSPV and a right inferior pulmonary vein RIPV, from the left atrium LA and the right atrium RA enables 80 to 90% of atrial fibrillations whose sources are in pulmonary veins to be completely cured.

In the meantime, when isolating an ostium of a vein using the balloon catheter system of the present embodiment, ablation effect can be enhanced by closing an atria side thereof, using a blood flow blocking balloon. Besides, when isolating a septulum, the ablation effect can be further enhanced through concomitant use of the blood flow blocking balloon at an opposite side of the septulum.

As described above, the balloon catheter system According to the present embodiment includes the catheter shaft 1 comprising the outer tube 2 and the inner tube 3, the balloon 6 provided between the distal portion 4 of the outer tube 2 and the distal portion 5 of the inner tube 3, the radiofrequency electrode 7 acting as the heating element provided inside the balloon 6, the thermocouple 8 acting as the temperature sensor which detects the temperature inside the balloon 6, the solution transport path 9 which is formed between the outer tube 2 and the inner tube 3 to communicate with the inside of the balloon 6, the vibration generator 42 which applies the vibrational wave C to the balloon 6 through the solution transport path 9, and further the vibrational wave baffle 10 which deflects the vibrational wave inside the balloon 6. Hence, the solution inside the balloon 6 is agitated by the vibrational wave C deflected to thereby permit the temperature distribution of the solution inside the balloon 6 to be uniformized. Further, the balloon 6 includes the contact portion 11 that is to contact the target site A and the noncontact portion 12 that is not to contact the target site A, wherein the membrane thickness of the contact portion 11 is thinner than that of the noncontact portion 12. As a result, the target site A that has come in contact with the thin contact portion 11 is selectively heated, while heat is hard to leak from the thick noncontact portion 12, so that only the target site A can be efficiently and uniformly ablated.

Further, the balloon 6 is formed in conformity to the shape of the target site A. Hence, the balloon 6 can be brought into close contact with the target site A without fail with the balloon 6 matched with the shape of the target site A.

Furthermore, the balloon 6 is substantially sphere-shaped or substantially onion-shaped. Besides, the contact portion 11 is provided in the vicinity of the distal portion of the balloon. Hence, the target site A can be ablated in the vicinity of the distal portion of the balloon 6.

Moreover, the outer tube 2 and the inner tube 3 are mutually slidable such that by varying the distance between the distal portion 4 of the outer tube 2 and the distal portion 5 of the inner tube 3, the length of the balloon 6 is changed, while by varying the pressure of the solution fed to the balloon 6, the diameter of the balloon 6 is changed. Hence, the balloon 6 can be changed in respect of both length and in diameter in conformity to the shape of the target site A, enabling the balloon 6 to be brought into close contact with the target site A.

Further, at the proximal portion of the catheter shaft 1, there is provided the distance regulating device 21 that regulates the distance between the distal portion 4 of the outer tube 2 and the distal portion 5 of the inner tube 3. Hence, the length of the balloon 6 can be regulated.

Also, the distance regulating device 21 includes the internally threaded portion 22 fixed to the proximal portion 16 of the outer tube 2, the fixing valve 23 that is provided inside the internally threaded portion 22 and has the inner tube 3 inserted therethrough, the rotating knob 25 provided with the externally threaded portion 24 which engages with the internally threaded portion 22 to tighten the fixing valve 23. Then, when the rotating knob 25 is rotated to tighten the fixing valve 23, the fixing valve 23 is elastically deformed in order for the inner tube 3 to be fixed to the internally threaded portion 22. Hence, with the operation thus simplified, the inner tube 3 can be fixed to an appropriate position relative to the outer tube 2.

Furthermore, the distance regulating device 21 includes the indicating needle 26 fixed to the inner tube 3 inside the rotating knob 25, and the rotating knob is formed in a frame shape and a movable range of the indicating needle 26 is limited within the internal side of the rotating knob 25. Hence, the movable range of the inner tube 3 in relation to the outer tube 2 can be kept within an appropriate range.

Moreover, the rotating knob 25 is provided with the scale 28 indicating the distance between the distal portion 4 of the outer tube 2 and the distal portion 5 of the inner tube 3 according to a position of the indicating needle 25. Hence, the length of the balloon 6 can be precisely set.

In addition to the foregoing, there are provided the first lead wire 33 connected to the radiofrequency electrode 7 acting as the heating element and the second lead wire 34 connected to the temperature sensor 8; the radiofrequency electrode 7 and the thermocouple 8 are fixed to the distal portion 5 of the inner tube 3; and between the distal portion 5 and proximal portion 17 of the inner tube 3, the first lead wire 33 and the second lead wire 34 are fixed to the inner tube 3. Hence, when the outer tube 2 and the inner tube 3 are allowed to slide with each other, the first wire 33 and the second wire 34 can be prevented from becoming entwined with each other.

Embodiment 2

Figure 6:
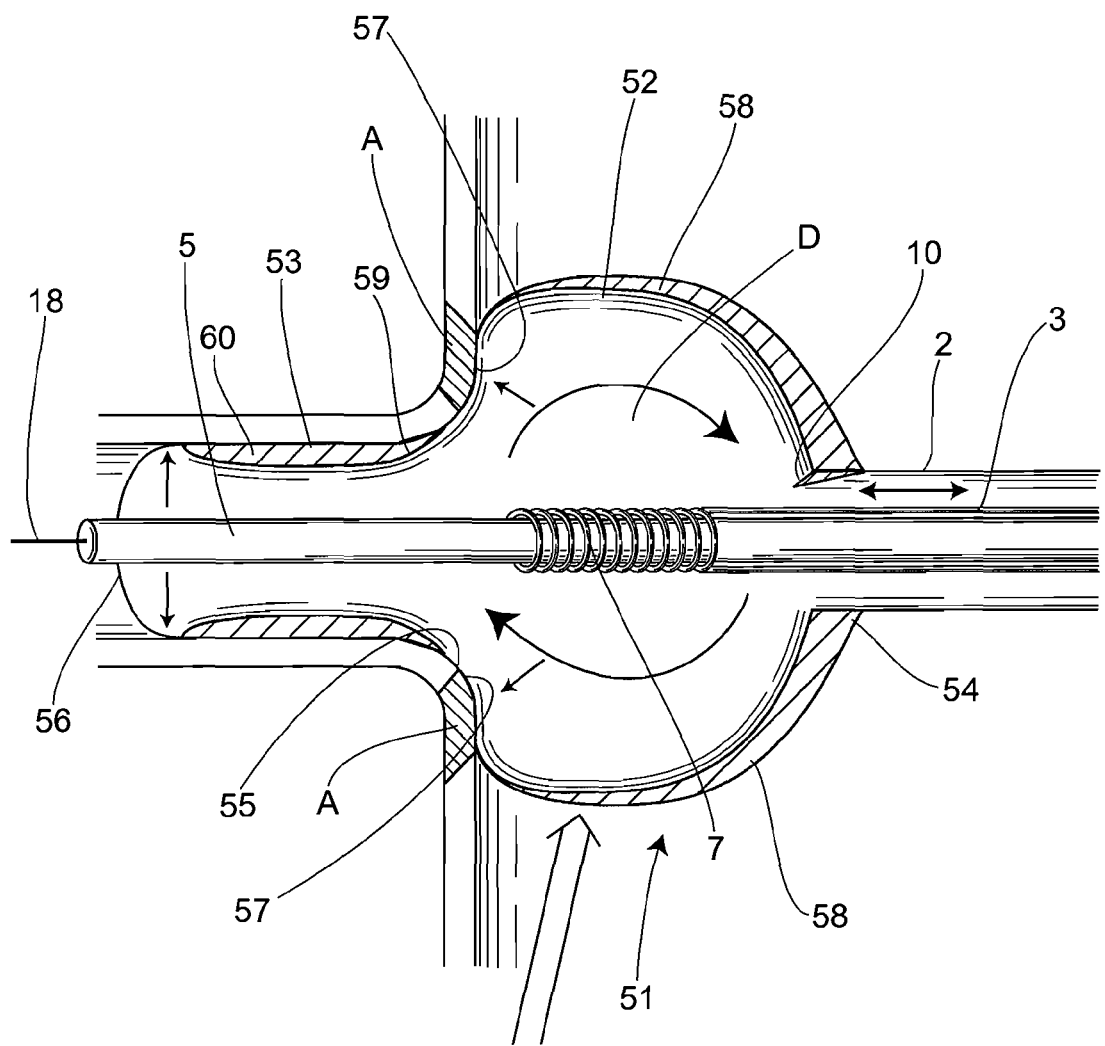
FIG. 6 is a partially enlarged view showing the vicinity of a balloon of a balloon catheter system according to a second embodiment of the present invention.

In FIG. 6 is shown a second embodiment of a balloon catheter system according to the present invention, in which the same numeral symbols are used for parts the same as in the first embodiment and a detailed description thereof is omitted.

The catheter system according to the present embodiment is the same as in the above first embodiment except that the balloon catheter system thereof includes a balloon 51 of a shape suitable for electrically isolating the ostium of the left inferior pulmonary vein LIPV and the ostium of the right inferior pulmonary vein RIPV.

The balloon 51 comprises a spherical portion 52 having a substantially spherical contour and a cylindrical portion 53 having a substantially cylindrical contour. The radiofrequency electrode 7 is located at a center of the spherical portion 52. A proximal portion 54 of the spherical portion 52 is fixed to the distal portion 4 of the outer tube 2. The cylindrical portion 53 that is formed integrally with the spherical portion 52 and in conformity to a shape of the pulmonary vein is provided in a manner extending from a distal portion 55 of the spherical portion 52. Further, a distal portion 56 of the cylindrical portion 53 is fixed to the distal portion 5 of the inner tube 3 with an inside of the cylindrical portion 53 communicating with an inside of the spherical portion 52. In addition, the spherical portion 52 is formed so as to have an outside diameter more than twice that of the cylindrical portion 53.

The spherical portion 52 of the balloon 6 includes a contact portion 57 that is to contact the target site A in an ostium of a pulmonary vein and a noncontact portion 58 that is not to contact the target site A. A membrane thickness of the contact portion 57 is thinner than that of the noncontact portion 58. In the vicinity of the distal portion of 55 of the spherical portion 52, the contact portion 57 is formed around a portion from which a proximal portion 59 of the cylindrical portion 53 extends. The balloon 51 is formed from synthetic resin such as polyurethane or the like. The contact portion 57 is formed to a 0.1 to 0.2 mm membrane thickness, while the noncontact portion 58 is formed to a 0.2 to 0.4 mm in membrane thickness. With the structure thus made, heat inside the balloon 51 can be prevented from leaking from the noncontact portion 58 to the outside, and thus only the target site A that has come in contact with the contact portion 57 can be effectively heated and ablated.

Besides, a membrane thickness of the distal portion 56 of the cylindrical portion 53 is formed thinner than those of the proximal portion 59 of the cylindrical portion 53 and central portion 60. Then, by pressurizing an inside of the balloon 51, the distal portion 56 of the cylindrical portion 53 is inflated, so that the cylindrical portion 53 is held in a fixed position inside a pulmonary vein. The balloon 51 is formed in conformity to the shape of the target site A in the ostium of the pulmonary vein or the contour of the pulmonary vein to hold the distal portion 56 of the cylindrical portion 53 in a fixed position inside the pulmonary vein. As a result, the balloon 51 is brought into close contact with the target site A to completely block off the blood flow in the ostium of the pulmonary vein, thus enabling the target site A to be effectively heated.

By taking advantage of the balloon catheter system of the present embodiment, the ostium of the left inferior pulmonary vein LIPV and the ostium of the right inferior pulmonary vein RIPV can be easily and electrically isolated without developing complications.

As described above, according to the balloon catheter system of the present embodiment, the balloon 51 comprises the spherical portion 52 fixed to the distal portion 4 of the outer tube 2 and the cylindrical portion 53 that is extended from the spherical portion 52 and is fixed to the distal portion 5 of the inner tube 3. Further, the contact portion 57 is provided in the vicinity of the distal portion 55 of the spherical portion 52, and besides the distal portion 56 of the cylindrical portion 53 is formed thinner than the proximal portion 59 of the cylindrical portion 53. Hence, by pressurizing the inside of the balloon 51, the distal portion 56 of the cylindrical portion 53 is inflated to fix the cylindrical portion 53 to the inside of the blood vessel without fail, thus enabling the target site A in a circumferential portion of the ostium of the blood vessel to be ablated reliably by the contact portion 57 provided in the vicinity of the distal portion 55 of the spherical portion 52.

Embodiment 3

Figure 7:
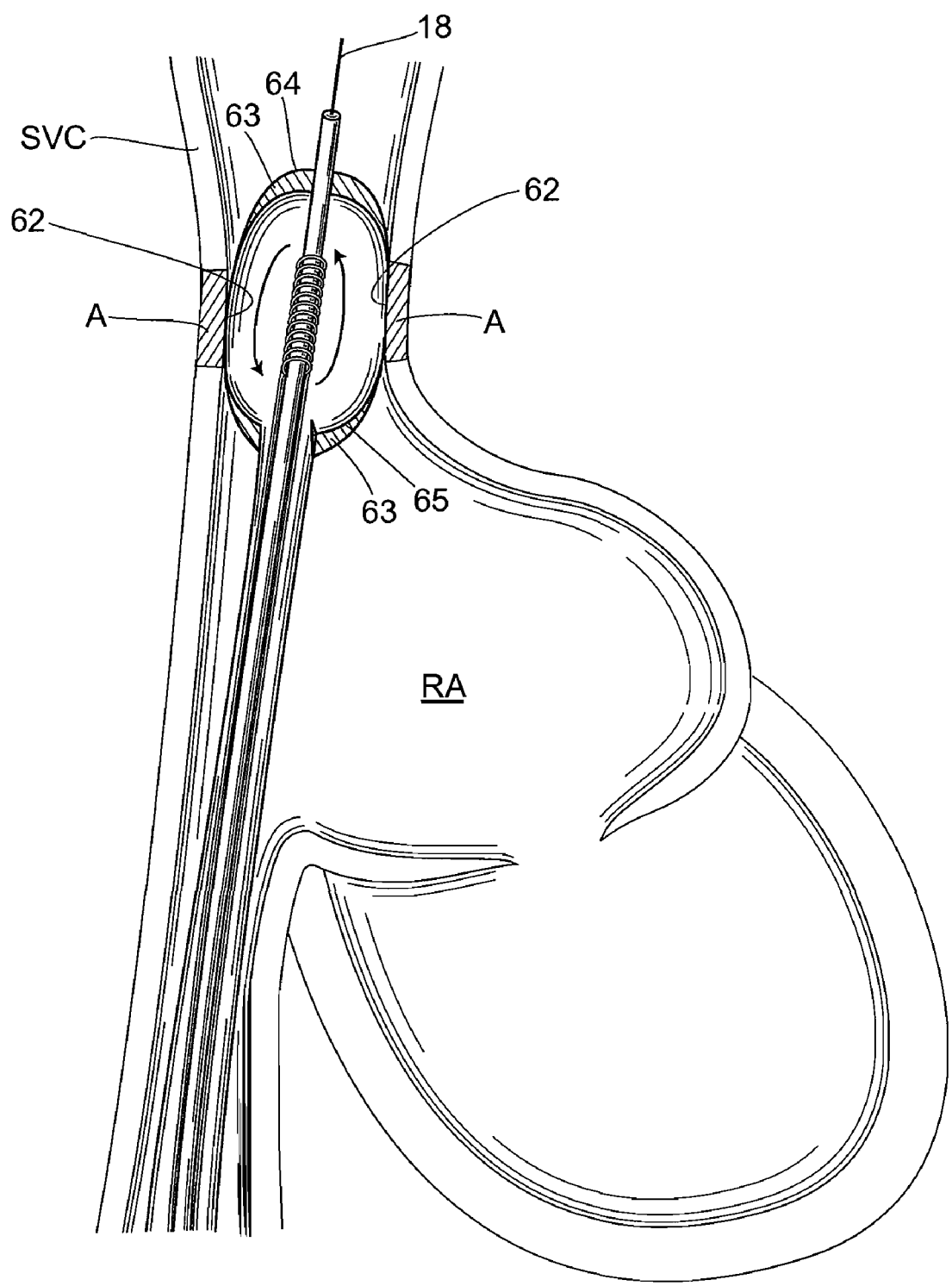
FIG. 7 is a partially enlarged view showing the vicinity of a balloon of a balloon catheter system according to a third embodiment of the present invention.

In FIG. 7 is shown a third embodiment of a balloon catheter system according to the present invention, in which the same numeral symbols are used for parts the same as in the first embodiment and a detailed description thereof is omitted.

A balloon catheter system according to the present embodiment is the same as the above first embodiment except that a balloon 61 has a shape suitable for electrically isolating an ostium of a superior vena cava SVC.

The balloon 61 is formed in a substantially cylindrical shape, including a contact portion 62 that is to come in contact with a target site A of the ostium of the superior vena cava SVC and a noncontact portion that is not to contact the target site A. A membrane thickness of the contact portion 62 is less than that of the noncontact portion 63. The contact portion 62 is provided in the vicinity of a center of the balloon 61, while the noncontact portion 63 is formed in the vicinity of a distal portion 64 of the balloon 61 and in the vicinity of a proximal portion 65 thereof. The balloon 61 is formed from synthetic resin such as polyurethane or the like. The contact portion 62 and the noncontact portion 63 are formed to a 0.1 to 0.2 mm thickness and a 0.2 to 0.4 mm thickness, respectively. With the structure thus made, heat inside the balloon 61 can be prevented from leaking from the noncontact portion 63, permitting only the target site A that has come in contact with the contact portion 62 to be effectively ablated. Further, by forming the balloon 61 in conformity to the ostium of the superior vena cava SVC, the balloon 61 is allowed to be brought into close contact with the target site A while completely blocking off a blood flow in the ostium of the superior vena cava SVC, thus enabling the target site A to be effectively heated.

By taking advantage of the balloon catheter system according to the present embodiment, an electrical isolation of the ostium of the superior vena cava SVC can be easily achieved, so that atrial fibrillations whose sources are in the ostium of the superior vena cava SVC can be completely cured.

As described above, according to the balloon catheter system of the present embodiment, the balloon 61 is substantially cylindrically-shaped, and the contact portion 62 is provided in the vicinity of the central portion of the balloon 61. Hence, the target site A can be ablated in the vicinity of the central portion of the balloon 61.

Embodiment 4

Figure 8:
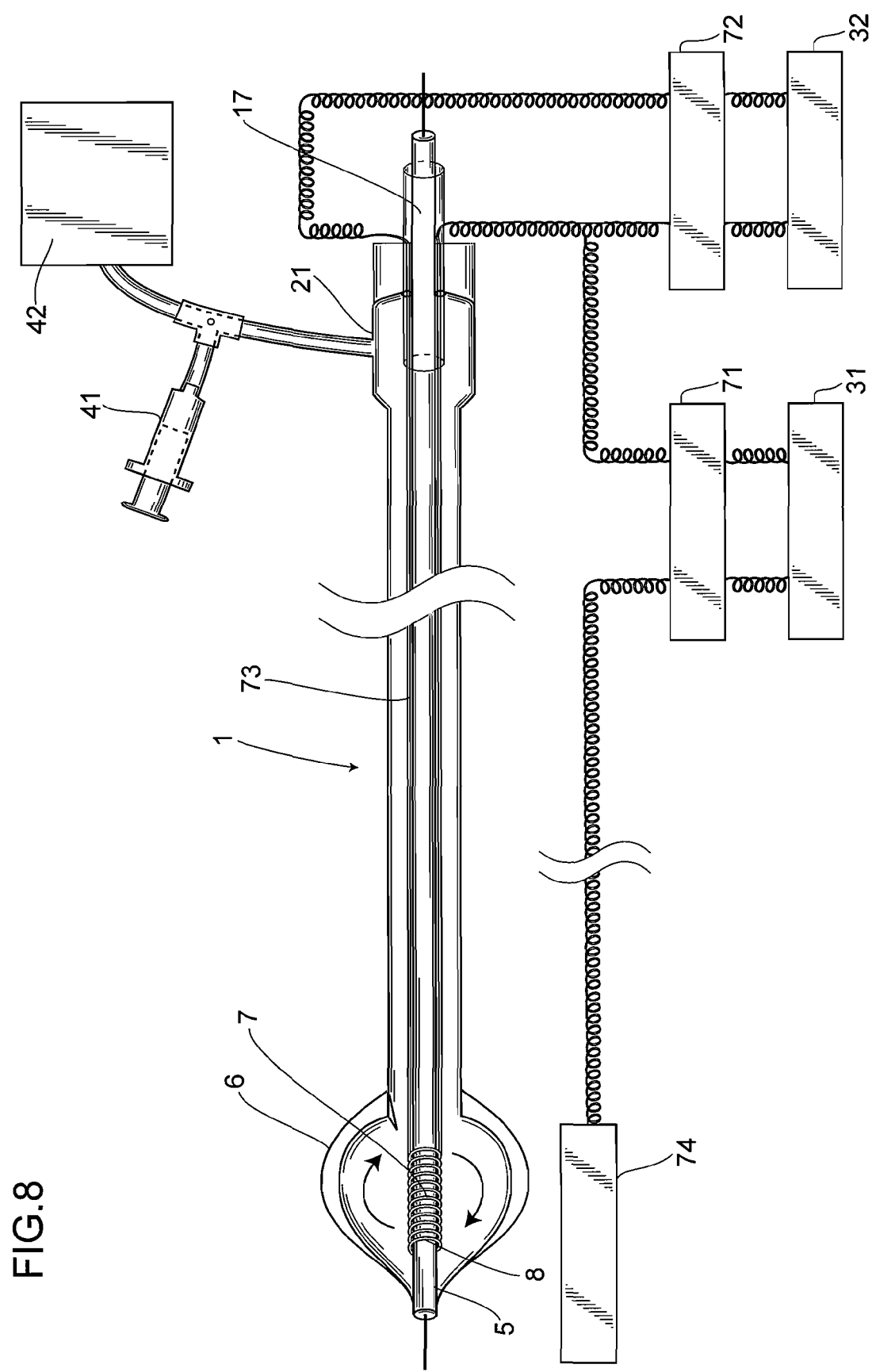
FIG. 8 is an overall view illustrating a balloon catheter system according to a fourth embodiment of the present invention.

In FIG. 8 is shown a fourth embodiment of a balloon catheter system according to the present invention, in which the same numeral symbols are used for parts the same as in the first embodiment and a detailed description thereof is omitted.

The balloon catheter system according to the present embodiment is the same as the first embodiment except that an electrical system thereof is different.

The radiofrequency generator 31 is connected with a low-frequency band cut filter 71 which cuts low-frequency components of the radiofrequency waves output from the radiofrequency generator 31. Further, the thermometer 32 is connected with a radiofrequency band cut filter 72 which cuts radiofrequency components input to the thermometer 32. There are provided two lead wires 73 extending from the proximal portion 17 of the inner tube 2 to the distal portion 5 thereof along the inner tube 2, and these lead wires 73 are shared by the radiofrequency electrode 7 and the thermocouple 8. Specifically, the two lead wires connected with the thermocouple 8 are connected with the thermometer 32 via the radiofrequency band cut filter 72, while one of the lead wires 73 is further connected with the radiofrequency generator 31 via the low-frequency band cut filter 71. Further, a return electrode 74 feeding an electromagnetic wave to the radiofrequency electrode 7 is connected with the low-frequency band cut filter 71.

Then, radiofrequency currents output from the radiofrequency generator 31 are subjected to the cut of the low-frequency components by the low-frequency band cut filter 71 and then are fed to the radiofrequency electrode 7. Further, temperature electric signals detected by the thermocouple 8 are subjected to the cut of the radiofrequency components output from the radiofrequency generator 31 by the radiofrequency band cut filter 72 and then are input to thermometer 32. Accordingly, the lead wires 73 can be shared by the radiofrequency electrode 7 and the thermocouple 8 without the interference between the signals of the radiofrequency electrode 7 and the signals of the thermocouple 8 by using the radiofrequency band of electrical signals through the low-frequency band cut filter 71 as well as the low-frequency band thereof through the radiofrequency band cut filter 72.

As described above, the balloon catheter system according to the present embodiment includes the radiofrequency generator 31 which feeds radiofrequency power to the radiofrequency electrode 7, thermometer 32 which indicates the temperature detected by thermocouple 8, the low-frequency cut filter 71 which is provided between the radiofrequency electrode 7 and the radiofrequency generator 31 and cuts low-frequency components of the radiofrequency waves output from the radiofrequency generator 31, the radiofrequency cut filter 72 which is provided between the thermocouple 8 and thermometer 32 and cuts radiofrequency components input to the thermometer 32, and the lead wire 73 which connects the thermocouple 8 and the radiofrequency cut filter 72 with each other, whereby the radiofrequency power is fed to the radiofrequency electrode 7 through the lead wire 73. Hence, only the radiofrequency components are output from the radiofrequency generator 31, while only the low-frequency components are input from the radiofrequency generator 31 to the thermometer 32, and thus the lead wire 73 for the radiofrequency electrode 7 and thermocouple 8 is shared to enable the radiofrequency power supply and the temperature detection to be performed at the same time.

Embodiment 5

Figure 9:
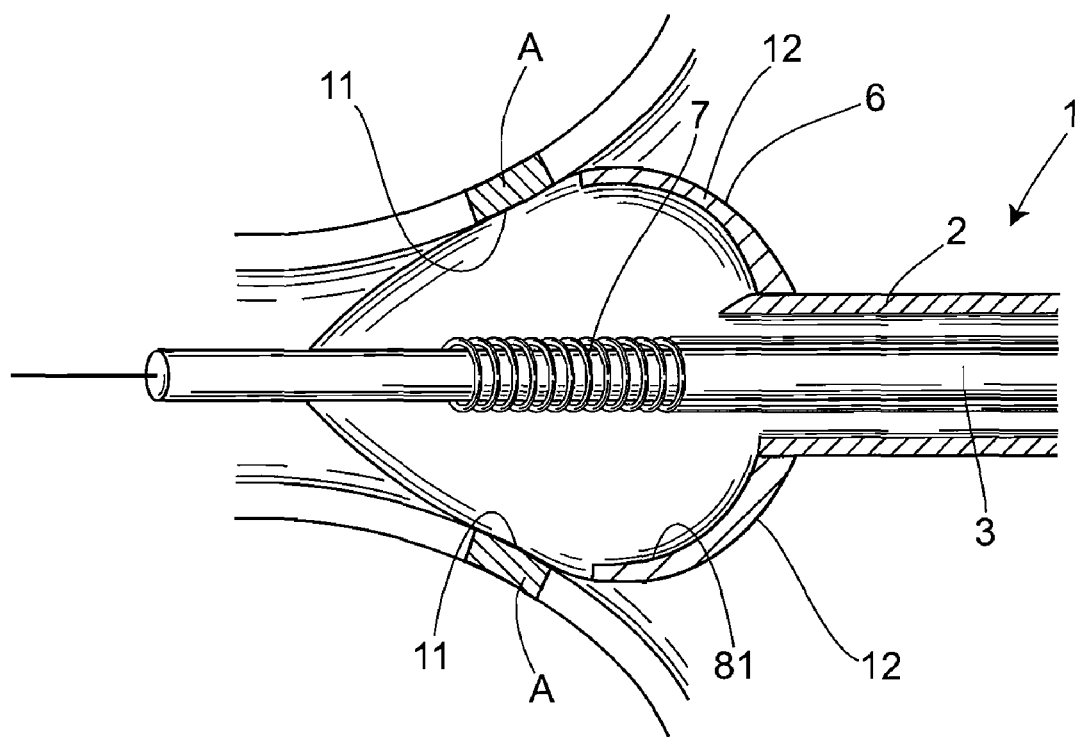
FIG. 9 is a partially enlarged view showing the vicinity of a balloon of a balloon catheter system according to a fifth embodiment of the present invention.

In FIG. 9 is shown a fifth embodiment of a balloon catheter system according to the present invention, in which the same numeral symbols are used for parts the same as in the first embodiment and a detailed description thereof is omitted.

The balloon catheter system according to the present embodiment is the same as the above first embodiment except that it employs a different structure for a membrane of the balloon 6.

In the balloon 6, the noncontact portion 12 is formed to a 0.1 to 0.2 mm thickness that is the same as that of the contact portion but the noncontact portion 12 is coated with a heat insulation layer 81. With the structure thus made, heat inside the balloon 6 can be prevented from leaking out of the noncontact portion 12, permitting only the target site A that has come in contact with the contact portion 11 to be effectively ablated.

As described above, according to the balloon catheter system of the present embodiment, the balloon 6 includes the contact portion 11 that is to contact the target site A and the noncontact portion 11 that is not to contact the target site A, and the heat insulation layer 81 is provided in the noncontact portion 12. Hence, heat is hard to leak from the noncontact portion 12, thereby permitting only the target site A to be efficiently and selectively ablated.

In the meantime, the present invention is not limited to the foregoing embodiments and various modifications are possible within the scope of the gist of the present invention. For example, whilst the foregoing embodiments refer to the balloon catheter system for electrical isolation of the specific site: the ostium of the pulmonary vein for treatment of the atrial fibrillation, the balloon catheter system of the invention may be used for treatment of any other sites. With respect to a shape of the balloon as well, it is not limited to those described above, but the balloon may be formed in a wide variety of shapes depending on sites to be cured.

The invention claimed is:

1. A balloon catheter system comprising:
    a catheter shaft comprising an outer tube and an inner tube;
    an elastic balloon provided between a distal end of said outer tube and a vicinity of a distal end of said inner tube;
    a heating element provided inside said balloon;
    a temperature sensor which detects a temperature inside said balloon;
    a solution transport path formed between said outer tube and said inner tube, in communication with an inside of said balloon;
    a vibration generator which applies vibrational waves to said balloon through said solution transport path; and
    a vibrational wave baffle which deflects said vibrational waves inside said balloon,
    wherein said balloon includes a contact portion that is to contact a target site and a noncontact portion that is not to contact said target site, said contact portion having a membrane thickness less than that of said noncontact portion, while said balloon is substantially sphere-shaped or onion-shaped, and said contact portion is provided in the vicinity of the distal portion of said balloon.

2. The balloon catheter system according to claim 1, wherein said heating element is any one of a radiofrequency electrode, a nichrome wire, an infrared ray generator, a heat emitting diode, a laser irradiator and an ultrasonic wave generator.

3. The balloon catheter system according to claim 1, wherein said balloon is formed in conformity to a shape of a target site.

4. The balloon catheter system according to claim 1, wherein said outer tube and said inner tube are constituted in a manner capable of sliding with each other so that a length of said balloon is changed by varying a distance between the distal end of said outer tube and the distal end of said inner tube, while a diameter of said balloon is changed by varying pressure of solution supplied to said balloon.

5. The balloon catheter system according to claim 4, further comprising a first lead wire connected to said heating element and a second lead wire connected to said temperature sensor, wherein said heating element and said temperature sensor are fixed to the distal end of said inner tube, while said first lead wire and said second lead wire are fixed to said inner tube between the distal end of said inner tube and the proximal portion thereof.

6. The balloon catheter system according to claim 1, further comprising a distance regulating device provided at a proximal portion of said catheter shaft, said distance regulating device regulating a distance between the distal end of said outer tube and the distal end of said inner tube.

7. The balloon catheter system according to claim 6, wherein said distance regulating device includes an internally-threaded portion fixed to a proximal end of said outer tube, a fixing valve that is provided inside said internally-threaded portion and has said inner tube inserted therethrough, and a rotating knob provided with an externally-threaded portion which engages with said internally-threaded portion and tightens said fixing valve, whereby said fixing valve is elastically deformed when said rotating knob is rotated to tighten said fixing valve so that said inner tube is fixed to said internally-threaded portion.

8. The balloon catheter system according to claim 7, wherein said distance regulating device includes an indicating needle fixed to said inner tube inside said rotating knob, said rotating knob being formed in a frame shape to limit a movable range of said indicating needle within an internal side of said rotating knob.

9. The balloon catheter system according to claim 8, wherein said rotating knob includes a scale that indicates the distance between the distal end of said outer tube and the distal end of said inner tube by means of a position of said indicating needle.

10. The balloon catheter system according to claim 1, wherein said heating element is a radiofrequency electrode, while said temperature sensor is a thermocouple, said balloon catheter system further comprising: a radiofrequency generator which feeds a radiofrequency current to said radiofrequency electrode; a thermometer which indicates a temperature detected by said thermocouple; a low-frequency band cut filter that is provided between said radiofrequency electrode and said radiofrequency generator and cuts off low-frequency components of the radiofrequency waves output from said radiofrequency generator; a radiofrequency band cut filter that is provided between said thermocouple and said thermometer and cuts off radiofrequency components input to said thermometer; and a lead wire that connects said thermocouple with said radiofrequency band cut filter, whereby said radiofrequency current is fed to said radiofrequency electrode through said lead wire.

11. A balloon catheter system comprising:
   a catheter shaft comprising an outer tube and an inner tube;
   an elastic balloon provided between a distal end of said outer tube and a vicinity of a distal end of said inner tube;
   a heating element provided inside said balloon;
   a temperature sensor which detects a temperature inside said balloon;
   a solution transport path formed between said outer tube and said inner tube, in communication with an inside of said balloon;
   a vibration generator which applies vibrational waves to said balloon through said solution transport path; and
   a vibrational waves baffle which deflects said vibrational wave inside said balloon,
   wherein said balloon includes a contact portion that is to contact a target site and a noncontact portion that is not to contact said target site, said contact portion having a membrane thickness less than that of said noncontact portion, and
   wherein said balloon includes a spherical portion fixed to the distal end of said outer tube and a cylindrical portion that extends from said spherical portion and is fixed to the distal end of said inner tube, while said contact portion is provided in the vicinity of the distal portion of said spherical portion, and said cylindrical portion is formed to have a smaller membrane thickness at the distal portion thereof than at the proximal portion thereof.

* * * * *